(12) United States Patent
Miyamoto et al.

(10) Patent No.: US 7,629,166 B2
(45) Date of Patent: Dec. 8, 2009

(54) MEASURING APPARATUS FOR INTERACTION OF BIOMOLECULE

(75) Inventors: Tetsuro Miyamoto, Kasumigaura (JP); Hiroyuki Takei, Hatoyama (JP); Shigenori Togashi, Abiko (JP); Ryo Miyake, Tsukuba (JP)

(73) Assignee: Hitachi, Ltd., Tokyo (JP)

( * ) Notice: Subject to any disclaimer, the term of this patent is extended or adjusted under 35 U.S.C. 154(b) by 282 days.

(21) Appl. No.: 11/214,948

(22) Filed: Aug. 31, 2005

(65) Prior Publication Data
US 2007/0238162 A1    Oct. 11, 2007

(30) Foreign Application Priority Data
Sep. 27, 2004    (JP)    ............................. 2004-279797

(51) Int. Cl.
*C12M 1/34*    (2006.01)
(52) U.S. Cl. .................. 435/288.5; 435/288.7; 435/4; 436/525; 356/36; 356/451; 356/477
(58) Field of Classification Search .............. 435/283.1, 435/287.1, 4, 288.7; 436/525; 356/36, 451, 356/477
See application file for complete search history.

(56) References Cited

U.S. PATENT DOCUMENTS 6,331,276 B1 *  12/2001  Takei et al. .............. 422/82.09
6,773,926 B1    8/2004   Fruend et al.

FOREIGN PATENT DOCUMENTS

| JP | 10-339808 | 12/1998 |
|---|---|---|
| JP | 11-1703 | 1/1999 |
| JP | 11-326193 | 11/1999 |
| JP | 2000-55920 | 2/2000 |
| JP | 2002-228662 | 8/2002 |
| JP | 2002-365210 | 12/2002 |
| WO | WO 01/35081 | 5/2001 |
| WO | WO 2004/059279 | 7/2004 |

OTHER PUBLICATIONS

Journal of Structural Biology 127, Feb. 1999 "Metallosomes", Hainfeld et al, pp. 152-160.
High Density Synthetic Oligonucleotide arrays, Lipshutz et al, Review, Nature Genetics Suppl, vol. 21, Jan. 1999.
"Exploring The new World Of The Genome With DNA Microarrays", Brown e tal, Nature Genetics Supplement, vol. 21, Jan. 1999, pp. 33-37.

* cited by examiner

*Primary Examiner*—Nelson Yang
(74) *Attorney, Agent, or Firm*—Antonelli, Terry, Stout & Kraus, LLP.

(57) ABSTRACT

In a measuring apparatus for biomolecule interaction, a fine particle sensor surface is dipped in a buffer solution in a reaction vessel to conduct spectral measurement by way of optical fibers. The buffer solution in the reaction vessel is made to enter an upper reaction vessel and discharged from a flow channel. Air is injected from a flow channel to inject a specimen from the discharge port to the reaction vessel. Then the specimen is sucked into the reaction vessel and brought into contact with the sensor surface where a ligand and an analyte in the specimen are bonded. Bonding is measured by a spectrophotometer through the optical fibers. A buffer solution is injected from the injection flow channel into the reaction vessel and the specimen is discharged out of the flow channel. The dissociation process in which the biomolecules are dissociated along with lowering of the concentration is measured.

8 Claims, 4 Drawing Sheets

MEASURING APPARATUS FOR INTERACTION OF BIOMOLECULE

The present application claims priority from Japanese application JP2004-279797 filed on Sep. 27, 2004, the content of which is hereby incorporated by reference into this application.

BACKGROUND OF THE INVENTION

The present invention concerns an apparatus for measuring the biomolecule interaction including a biosensor used in biochemical research, development of medicines, medical diagnosis, food inspection, etc.

In the existent measuring apparatus for biomolecules interaction, sensors utilizing a surface plasmon resonance method have been often used. The surface plasmon is compressive waves of free electrons propagating along the boundary between a metal thin film and a dielectric material and since this is greatly affected by the dielectric constant at the boundary, deposition of molecules to the surface can be detected by detecting the dielectric constant, which is used for the detection principle of immunosensors, gas sensors, etc.

However, since the surface plasmon resonance sensor has a complicate structure, Japanese Patent Laid-Open No. 2000-55920 proposes a sensor capable of measurement in a simple optical system as a fine noble metal sensor compared with the surface plasmon resonance sensor. A specific example of the fine noble metal sensor is described in Japanese Patent Laid-Open No. H11(1999)-1703. In this laid-open publication, fine particles such as of polymer, $SiO_2$, $TiO_2$, etc. is formed as a single layer on a noble metal thin film formed on a substrate, on which a noble metal such as gold, silver, copper, or platinum is vapor deposited or sputtered. This forms cap-shaped fine particles made of gold, silver, copper, platinum, etc. on fine particles. Another example of the fine noble metal particle sensor is described in Japanese patent Laid-Open No. H10(1998)-339808. This laid-open publication discloses that a substrate exhibits a remarkable color formation when fine noble metal particles are formed. The color formation is caused by absorption of a light for a portion of a wavelength region when a white light is reflected.

The absorption peak wavelength of the fine noble metal particles depends on the refraction index of the surface. Then, detection of the reaction that changes the refraction index of the surface is disclosed in Japanese Patent Laid-Open No. H11(1999)-326193. Further, Japanese Patent Laid-Open Nos. 2000-55920 and 2002-365210 describe that the surface can be modified by biomolecules having specific adsorption such as antibody and DNA, and utilized as a biosensor. Further, Japanese Patent Laid-Open No. 2002-228662 describes a biomolecule measuring apparatus at high sensitivity by utilizing fine noble metal particles.

In the measuring method of using the fine noble metal particle sensor described in each of the laid-open publications, fine noble metal particles modified by biomolecules are optically measured automatically. While the bonding of biobody molecules is measured as described above, no consideration has been taken for automatically depositing a liquid specimen or a buffer solution to fine metal particles. In a case where automatic optical measurement can be attained also including automatic deposition of the liquid specimen or the buffer solution to fine metal particles, a great amount of specimens can be treated in parallel by a small-sized apparatus in a short time.

BRIEF SUMMARY OF THE INVENTION

The present invention intends to provide a measuring apparatus for biomolecule interaction capable of automating optical measurement also including deposition of a liquid specimen and a buffer solution to fine metal particles and capable of treating a great amount of specimens in parallel in a short time by an apparatus of a reduced size.

A measuring apparatus for biomolecule interaction in accordance with the first aspect of the present invention includes a fine particle sensor device having a plurality of fine particle sensor surfaces in which fine noble metal particles are arranged, a plurality of reaction vessels capable of containing a buffer solution or a liquid specimen, a dipping device for dipping the fine particle sensor surface in the buffer solution or the liquid specimen contained in the reaction vessel, an optical measuring device for measuring optical characteristics of the fine particle sensor surface, and a light irradiation device for irradiating a light to the fine particle sensor surface dipped in the buffer solution or the liquid specimen and guiding a reflected light to the optical measuring device.

In a preferred embodiment, the bottom of the reaction vessel is formed of a transparent member, and a light from the light irradiation device is irradiated through the transparent member to the fine particle sensor surface. In a further preferred embodiment, the dipping device is adopted to move the reaction vessel for approaching or receding the reaction vessel to and from the fine particle sensor surface. In a further preferred embodiment, the fine particle sensor device has a specimen vessel for containing a specimen, and has a pressurizing device for pressurizing a gas to move the specimen contained in the specimen vessel to the reaction vessel.

In a further preferred embodiment, the reaction vessel has a buffer solution injection flow channel for injecting a buffer solution to the reaction vessel and a discharge flow channel for discharging the buffer solution or the liquid specimen contained in the reaction vessel to the outside of the reaction vessel. The fine particle sensor surface is inserted into the reaction vessel. The pressurizing device moves the specimen contained in the specimen vessel to the reaction vessel, and discharges the same from the discharge flow channel to the outside of the reaction vessel. The buffer solution contained in the reaction vessel may be replaced with the liquid specimen as described above.

In a further preferred embodiment, after the buffer solution is discharged from the discharge flow channel to the outside of the reaction vessel and replaced with the liquid specimen, the buffer solution is injected from the buffer solution injection flow channel to the reaction vessel to dissociate the biomolecules bonded to the fine particle sensor surface. The dissociation process may be measured by the optical measuring device receiving a light reflected from the fine particle sensor surface.

A measuring apparatus for biomolecule interaction in accordance with another aspect of the present invention includes a plurality of reaction vessels capable of containing a buffer solution or a liquid specimen and having a fine particle sensor surface in which fine noble metal particles are arranged on the bottom, a liquid specimen injection device for injecting a liquid specimen to the reaction vessel, a buffer solution injection flow channel for injecting the buffer solution to the reaction vessel, a discharge flow channel for discharging the buffer solution or the liquid specimen contained in the reaction vessel to the outside of the reaction vessel, and a light irradiation device guide having a light irradiation device of irradiating a light to the fine particle sensor surface dipped in the buffer solution or the liquid specimen and guiding a reflected light to an optical measuring device.

After the liquid specimen is contained in the reaction vessel, the buffer solution is injected from the buffer solution injection flow channel into the reaction vessel, while the liquid specimen in the reaction vessel is discharged by way of the discharge flow channel to the outside of the reaction vessel, the liquid specimen is replaced with the buffer solution to dissociate the biomolecules bonded to the fine particle sensor surface, and the dissociating process is measured by the optical measuring device receiving a light reflected from the fine particle sensor surface.

BRIEF DESCRIPTION OF THE SEVERAL VIEWS OF THE INVENTION

DETAILED DESCRIPTION OF THE INVENTION

The present invention is to be described by way of embodiments with reference to the appended drawings. The embodiments shown below have exchangeable fine particle sensors and specimen vessels corresponding thereto and can attain simultaneous measurement for a plurality of specimens in parallel.

Figure 1:
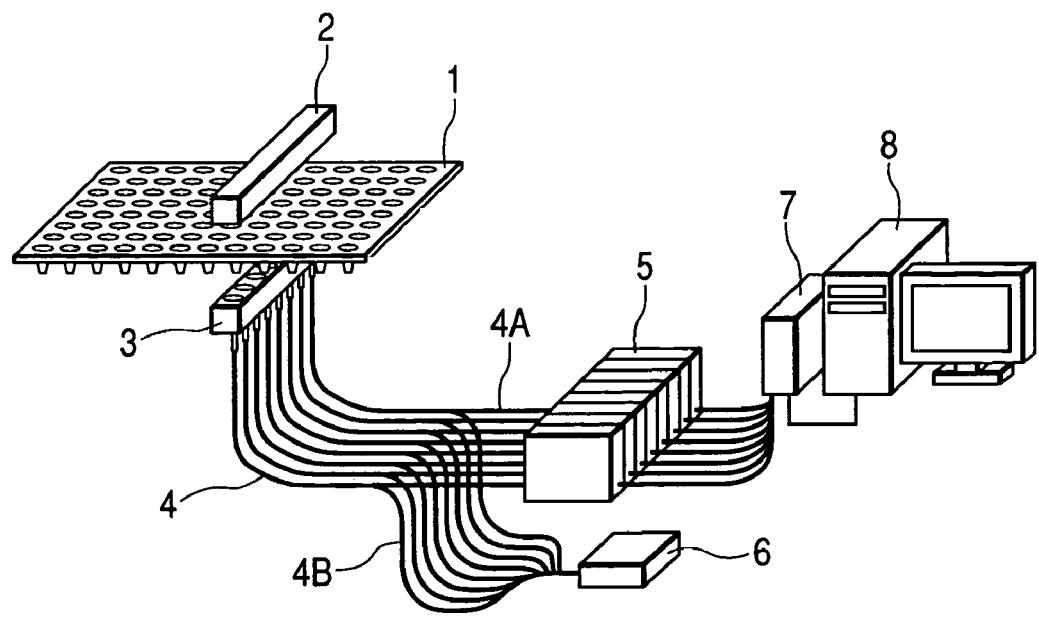
FIG. 1 is a perspective block diagram for one embodiment of a measuring apparatus for biomolecule interaction according to the present invention.

FIG. 1 shows a schematic entire constitutional view for one embodiment of a measuring apparatus for biomolecule interaction according to the invention. A sensor plate 1 has a plurality of wells (specimen vessels) for retaining specimens to be measured. In a case where the wells are arranged by the number and at an identical pitch identical with those in a multi-well plate used generally in the field of biochemistry, existent pretreatment devices, etc. can be utilized advantageously for the previous treatment such as dispensing of a specimen. In this embodiment, the sensor plate 1 has, for example, a 8-hole×12 row plate.

A pressurizing device 2 is located above and a reaction vessel 3 is located below the sensor plate 1. The pressurizing device 2 and the reaction vessel 3 correspond to one row of the sensor plate 1. In this embodiment, the pressurizing device 2 and the reaction vessel 3 have 8 pairs corresponding to the number of holes for the row of the sensor plate 1.

The pressurizing device 2 and the reaction vessel 3 are supported by a not-illustrated slide guide, etc. and they are movable in the direction in perpendicular to the surface of the sensor plate 1. Further, the sensor plate 1 is also supported by a not illustrated slide guide, etc. such that the sensor plate 1 can be moved horizontally (movement in the direction of the plane) to a direction perpendicular to the row (rightward and leftward in FIG. 1) corresponding to the pressurizing device 2 and the reaction vessel 3. Thus, the pressurizing device 2 and the reaction vessel 3 can sandwich an optional row of the sensor plate 1.

Further, optical fibers 4 are connected by the number of 8 to the lower portion of the reaction vessel 3 corresponding to one row of the sensor plate 1. The optical fibers 4 are branched into measuring optical fibers 4A and light source optical fibers 4B. The measuring optical fibers 4A are connected each to a 8-channel spectrophotometer 5 while the light source optical fibers 4B are connected each to a light source 6.

Accordingly, a light emitted from the light source 6 passes through the light source optical fibers 4B and is irradiated to a fine particle sensor surface 25 to be described later of the sensor plate 1 in the reaction vessel 3. Further, a reflection light from the fine particle sensor surface 25 of the sensor plate 1 reaches the spectrophotometer 5 by way of the optical fibers 4 and the measuring optical fibers 4A. The spectrophotometer 5 measures the absorption spectrum based on the reached reflection light, and the result for the measurement of the absorption spectrum is sent by way of an A/D converter 7 to a data processing device 8.

Figure 2:
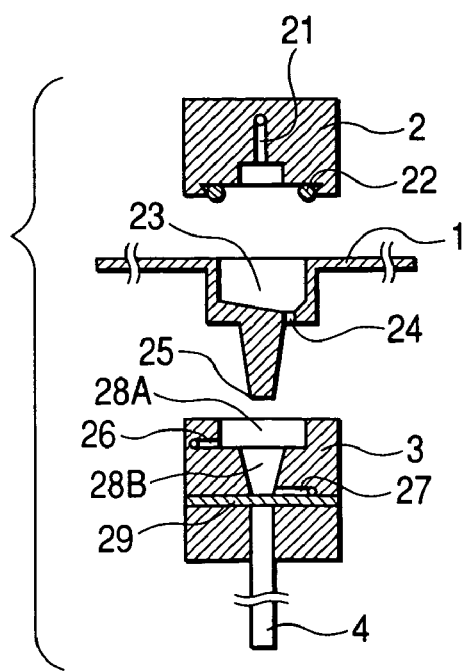
FIG. 2 is a longitudinal cross sectional view for a sensor plate provided to the apparatus.

Then, the detailed constitution for the sensor plate 1, the pressurizing device 2, and the reaction vessel 3 are to be described with reference to FIG. 2. FIG. 2 is a schematic cross sectional view for one well (hole) of the sensor plate 1 and the pressurizing device 2 and the reaction vessel 3 corresponding thereto. The sensor plate 1 has a specimen vessel 23 for retaining a specimen as a buffer solution (HEPES, PBS, etc.) containing biomolecules (analytes) as an object of measurement, a fine discharge port 24 for discharging the specimen, and a fine particle sensor surface 25 to which a light is irradiated. On the fine particle sensor surface 25, a single layer of fine particles such as of a polymer is formed, and a fine particle sensor formed of a noble metal in a cap-like shape is formed thereover.

Figure 7:
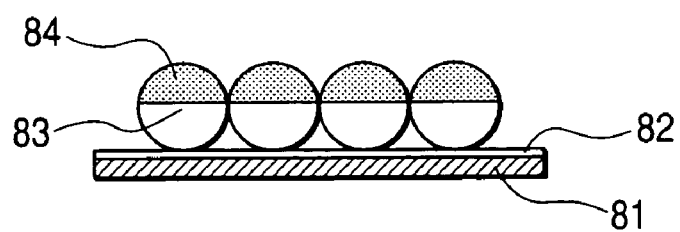
FIG. 7 is a front elevational view for an embodiment of a fine noble metal particle sensor according to the invention.

FIG. 7 shows details for the fine particle sensor. Fine particles 83 made of polymer, $SiO_2$, $TiO_2$, etc. are formed as a single layer on a thin noble metal film 82 formed to a substrate 81 and a noble metal such as gold, silver, copper, platinum, etc. is vapor deposited or sputtered. Thus, cap-like fine particles 84 made of gold, silver, copper, platinum, etc. are formed over the fine particles 83. Further, on the surface of the fine particle sensor surface 25, a chemical substance or biomolecule (ligand) that interacts with a biomolecule as an object of measurement is previously fixed.

The pressurizing device 2 has a pressurized air flow channel 21 for supplying air supplied from a not illustrated reservoir or pump to the specimen vessel 23 of the sensor plate 1, and a sealing O-ling 22 for sealing the face of contact between the pressurizing device 2 and the sensor plate 1 when the pressurizing device 2 is in contact with the sensor plate 1. Further, the reaction vessel 3 has an upper reaction vessel 28A, a lower reaction vessel 28B, a discharge flow channel 26 for discharging a liquid in the upper reaction vessel 28A, a buffer solution injection flow channel 27 for injecting a buffer solution to the lower reaction vessel 28B, and an optical measuring window 29 for transmitting a light for conducting optical measurement from the side of the bottom of the lower reaction vessel 28B.

A light emitted from the light source 6 passes from the optical fiber 4 and through the optical measuring window 29 and is irradiated to the fine particle sensor surface 25, and a portion of the reflected and scattered light from the fine particle sensor surface 25 returns again passing through the optical measuring window 29 to the optical fiber 4. Accordingly, it is preferred that the optical measuring window 29 is made of a transparent material such that it gives no undesired effects on the optical measurement.

Figure 3A:
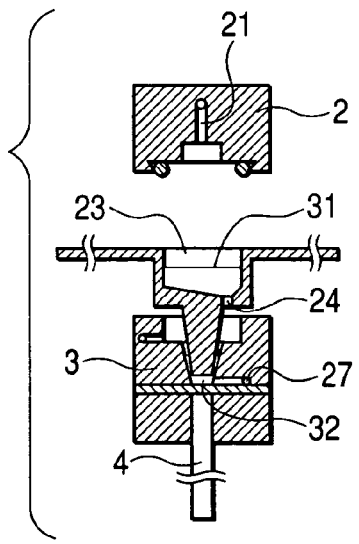
FIGS. 3A to 3C are views explaining the measuring operation.
Figure 3B:
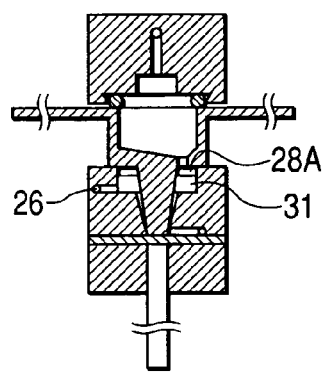
Figure 3C:
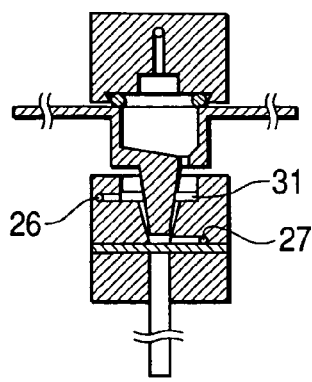

FIGS. 3A to 3C are views showing the operation of the sensor plate 1, the pressurizing device 2, and the reaction vessel 3 during measurement for biomolecule interaction. Before starting measurement, a liquid specimen 31 containing a biomolecules to be measured is injected to each of the specimen vessels 23 of the sensor plate 1 by using, for example, a pipette. The specimen 31 is retained in the specimen vessel 23 by a surface tension without being discharged from the specimen discharge port 24 so long as the specimen discharge port 24 is small enough and suction operation is not applied. Further, a buffer solution 32 is injected by way of a buffer solution injection flow channel 27 to the reaction vessel 3. Upon starting the measurement, as shown in FIG. 3A, the reaction vessel 3 is raised toward the specimen vessel 23 of the sensor plate 1, to dip the fine particle sensor surface 25 into the buffer solution 32 in the reaction vessel and then spectral measurement is started by using a light from the optical fiber 4.

Then, as shown in FIG. 3B, the reaction vessel 3 is further raised toward the specimen vessel 23 to extrude a most portion of the buffer solution 32 in the lower reaction vessel 28B to the upper reaction vessel 28A and then discharged from the discharge flow channel 26. Then, the pressurizing device 2 is lowered till it is in close contact with the sensor plate 1, air is injected from the pressurized air flow channel 21, and the specimen 31 is injected by the air pressure through the specimen discharge port 24 into the upper reaction vessel 28A.

Then, as shown in FIG. 3C when the reaction vessel 3 is lowered from the position shown in FIG. 3B to a position identical with the position shown in FIG. 3A, the specimen 31 in the upper reaction vessel 28A is sucked into the lower reaction vessel 28B, brought into contact with the fine particle sensor surface 25, and the ligand fixed on the fine particle sensor and the analyte in the specimen 31 are bonded. Depending on the degree of the bonding, the absorption spectrum of the fine particle sensor surface 25 changes, and the change is measured by the photo spectrometer through the optical fiber 4.

Finally, the buffer solution 32 is injected again from the buffer solution injection flow channel 27 to the lower reaction vessel 28B and a solution overflowed from the lower reaction vessel 28B is discharged form the discharge flow channel 26. In this case, the biomolecules bonded at the fine particle sensor surface 25 are dissociated along with lowering of the density. The dissociation process is also measured by the change of the absorption spectrum in the same manner as in the bonding process. The buffer solution 32 is injected and discharged sufficiently and after completing the cleaning of the specimen 31, the reaction vessel 3 is lowered to a initial position to complete measurement.

Figure 4A:
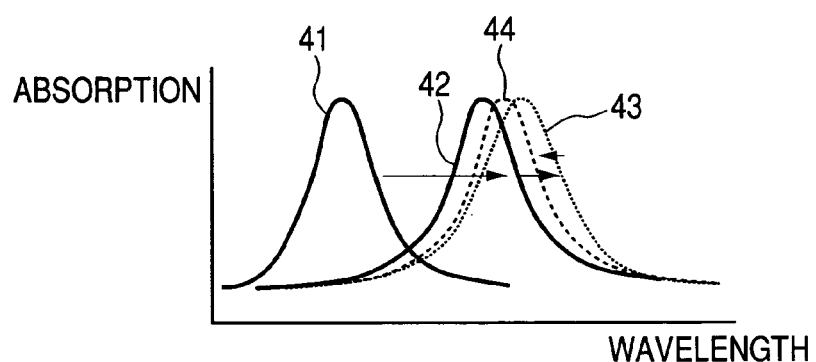
FIGS. 4A and 4B are graphs showing an example for the result of spectral measurement.
Figure 4B:
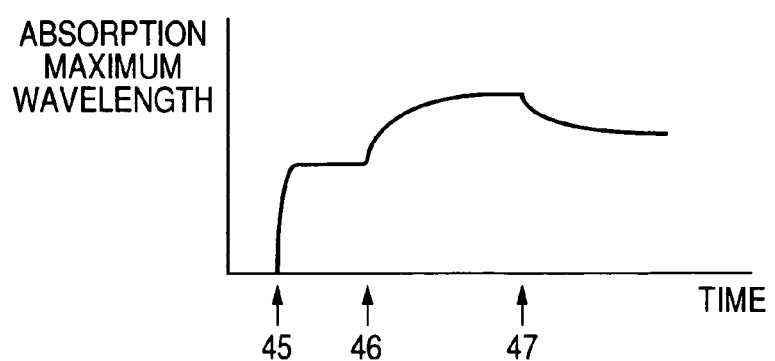

FIGS. 4A and 4B are graphs showing the data for the spectral measurement obtained in the data processing device 8. FIG. 4A is a graph showing the absorption spectrum obtained from the photo spectrometer 5 in which the wavelength is expressed on the abscissa and the light absorption is expressed on the ordinate. In the initial state, the fine particle sensor surface 25 is present in air and the absorption spectrum is as shown at 41. As described above, as a result of dipping the fine particle sensor surface 25 into the buffer solution 32, the absorption spectrum changes from 41 to 42. Further, when the buffer solution 32 in the lower reaction vessel 28B is replaced with the spectrum 31 and the biomolecules contained in the spectrum 31 are bonded with the ligand fixed on the fine particle sensor surface 25, the absorption spectrum changes from 42 to 43.

Then, when the buffer solution 32 is injected again from the buffer solution injection flow channel 27 to the lower reaction vessel 28B to replace the specimen 31 with the buffer solution 32 and dissociate the biomolecules and the ligand, the absorption spectrum changes from 43 to 44. FIG. 4B is a graph showing the change with time of the maximum absorption wavelength, among the changes of the absorption spectrum, in which time is expressed on the abscissa and the maximum absorption wavelength is expressed on the ordinate. Time 45 denotes the instance the fine particle sensor surface 25 is dipped in the buffer solution 32, the time 46 denotes the instance the buffer solution 32 in the lower reaction vessel 28B is replaced with the specimen 31, and the time 47 denotes the instance the specimen 31 is replaced with the buffer solution 32. The graph shows the degree of bonding of the biomolecules contained in the specimen 31 to the ligand on the fine particle sensor surface 25.

As described above, this embodiment includes the sensor plate 1 having the specimen vessel 23 for containing the liquid specimen, a protrusion having the fine particle sensor surface 25 in which fine particles are disposed at the top end face, and the specimen discharge port 24 for discharging the specimen contained in the specimen vessel downward.

Further, this embodiment includes the reaction vessel 3 having the upper reaction vessel 28A and the lower reaction vessel 28B containing the buffer solution 32 or the liquid specimen 31, the optical measuring window 29 forming the bottom of the lower reaction vessel 28B, the buffer solution injection flow channel 27 for injecting the buffer solution to the lower reaction vessel 28B and the discharge flow channel 26 for discharging the buffer solution 32 or the liquid specimen 31 contained in the upper reaction vessel 28A.

Further, the embodiment includes the pressurizing device 2 for supplying a pressure fluid to the specimen vessel 23 for injecting the specimen 31 contained in the specimen vessel 23 of the sensor plate 1 through the specimen discharge port 24 into the upper reaction vessel 28A of the reaction vessel 3. Further, the embodiment includes the optical fibers 4 for irradiating a light by way of the optical measuring window 29 of the reaction vessel 3 to the fine particle sensor surface 25 of the sensor plate 1 and guiding the reflection light from the fine particle sensor surface 25 to the photo spectrometer 5.

Then, the pressurizing device 2 is adopted to move vertically relative to the sensor plate 1 such that the pressurizing device 2 can be in close contact with the opening of the specimen vessel 23 of the sensor plate 1. The reaction vessel 3 is made movable vertically relative to the sensor plate 1 such that the fine particle sensor surface 25 can be inserted into the lower reaction vessel 28B of the reaction vessel 3. Further, the buffer solution 32 and the liquid specimen 31 are supplied and discharged interlocking with the vertical movement of the pressurizing device 2 and the reaction vessel 3 to the sensor plate 1.

Accordingly, this embodiment can provide a measuring apparatus for biomolecule interaction capable of automating optical measurement also including the deposition of the liquid specimen and the buffer solution to the fine metal particles and capable of processing a great amount of specimens in parallel in a short time although it is reduced in the size.

Figure 5:
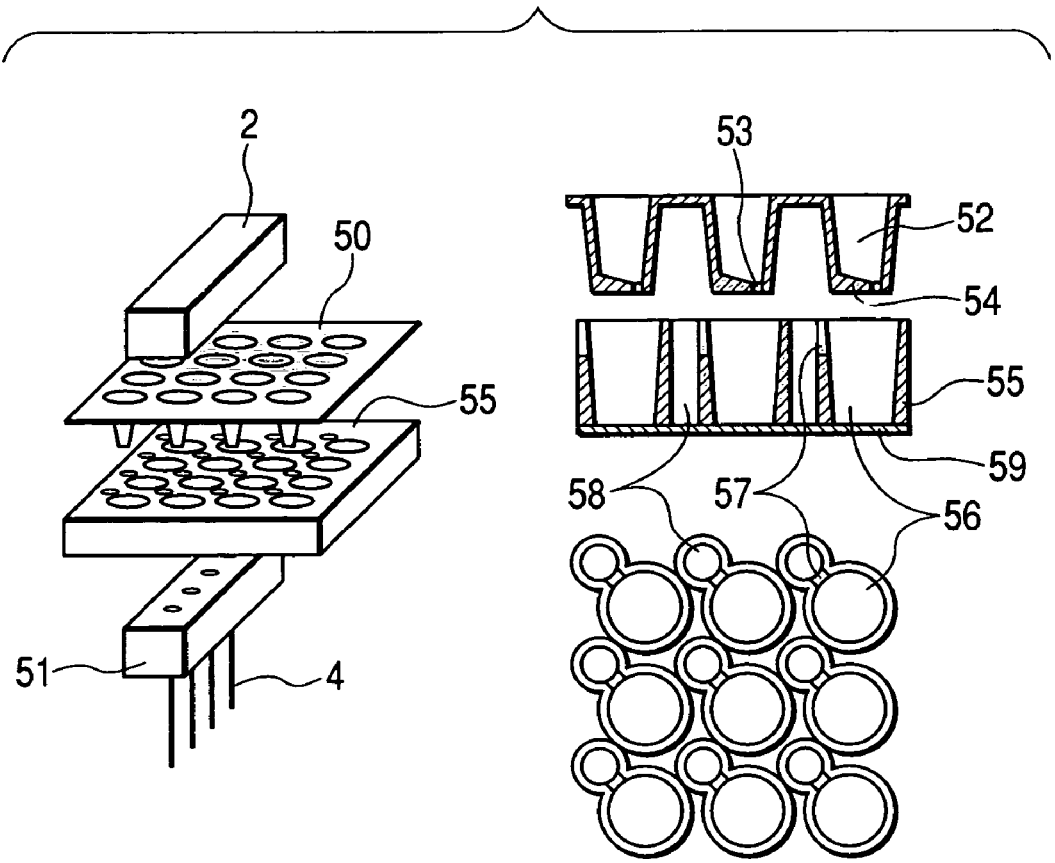
FIG. 5 is a longitudinal cross sectional view for another embodiment of a sensor plate according to the invention.

FIG. 5 shows, in a vertical cross sectional view, the peripheral portion of a sensor plate in another embodiment of the measuring apparatus for biomolecule interaction according to the invention. In this embodiment, a sensor plate 50 includes, like the embodiment described above, a specimen vessel 52, (corresponding to specimen vessel 23), a specimen discharge port 53, (corresponding to specimen discharge port 24), and a fine particle sensor surface 54 (corresponding to fine particle sensor surface 25).

This embodiment has a reaction vessel plate 55 to be paired with a sensor plate 50. The sensor plate 55 has reaction vessels 56, a discharge channels 57 for a buffer solution or specimen, and liquid discharge sumps 58 in which the bottom of the reaction vessel 56 constitutes an optical measuring window 59 made of a material of high transparency. Below the reaction vessel plate 55, optical fibers 4 like those attached to the reaction vessel 3 of the embodiment shown in FIG. 2 are arranged by an optical fiber holder 51.

The flow of the measurement in this embodiment is to be described briefly. In the initial state, a specimen 31 is injected in the specimen vessel 52, and a buffer solution 32 is previously injected into the reaction vessel 56. In this state, the sensor plate 50 and the reaction vessel plate 55 are previously stacked and disposed to the apparatus in a state where the fine particle sensor surface 54 is dipped in the buffer solution 32 in the reaction vessel 56, and measurement is started.

Successively, when the pressurizing plate 2 is brought into close contact with the opening of the specimen vessel 52 of the sensor plate 50 and air is discharged from the pressurizing device 2, the specimen 31 is injected passing through the specimen discharge port 53 into the reaction vessel 56. Thus, the buffer solution 32 in the reaction vessel 56 is discharged through the discharge channel 57 to the discharge liquid sump 58 and the inside of the reaction vessel 56 is replaced with the specimen 31. In this case, change of the absorption spectrum due to the bonding reaction of the biomolecules taken place at the fine particle sensor surface 54 is measured through the optical measuring window 59 and the optical fibers 4.

Also this embodiment can provide a measuring apparatus for biomolecule interaction capable of automating optical measurement also including the deposition of the liquid specimen and the buffer solution to the fine metal particles and capable of processing a great amount of specimens in parallel in a short time although it is reduced in the size. Further, different from the embodiment shown in FIG. 2, the portion in contact with the specimen 31 or the buffer solution 32 is the sensor plate 50 and the reaction vessel plate 55 in this embodiment, and all of the sensor plate 50 and the reaction vessel plate 55 can be replaced on every use. In the embodiment shown in FIG. 2, only the sensor plate 1 was replaced on every use. Accordingly, this embodiment has an advantage capable of further decreasing cross contamination during continuous measurement.

Different form the embodiment shown in FIG. 2, this embodiment can not measure the dissociation phenomenon by replacement with the buffer solution after bonding of the biomolecules. In view of the above, in another embodiment according to the invention, while identical in view of the basic constitution with that of the embodiment shown in FIG. 5, a specimen vessel 52 and a specimen discharge port 53 in the sensor plate 50 are bisected, so that two types of solutions can be retained. Also for the pressurizing device 2, two pressurized air injection ports are disposed such that pressure can be applied separately to two specimens. That is, a specimen is contained in one of the vessels divided from one specimen vessel 52, and a buffer solution for replacement is injected in the other of the vessels. Then, the buffer solution contained in the reaction vessel 56 of the reaction vessel plate 55 and the specimen contained in the specimen vessel 52 are replaced. Then, the buffer solution for replacement contained in the specimen vessel 52 is replaced with the specimen contained in the reaction vessel 56. With the constitution described above, the same effect as that of the embodiment shown in FIG. 5 can be obtained. Further, since replacement with the buffer solution is conducted after bonding of the biomolecules, the dissociation phenomenon can be measured.

Figure 6:
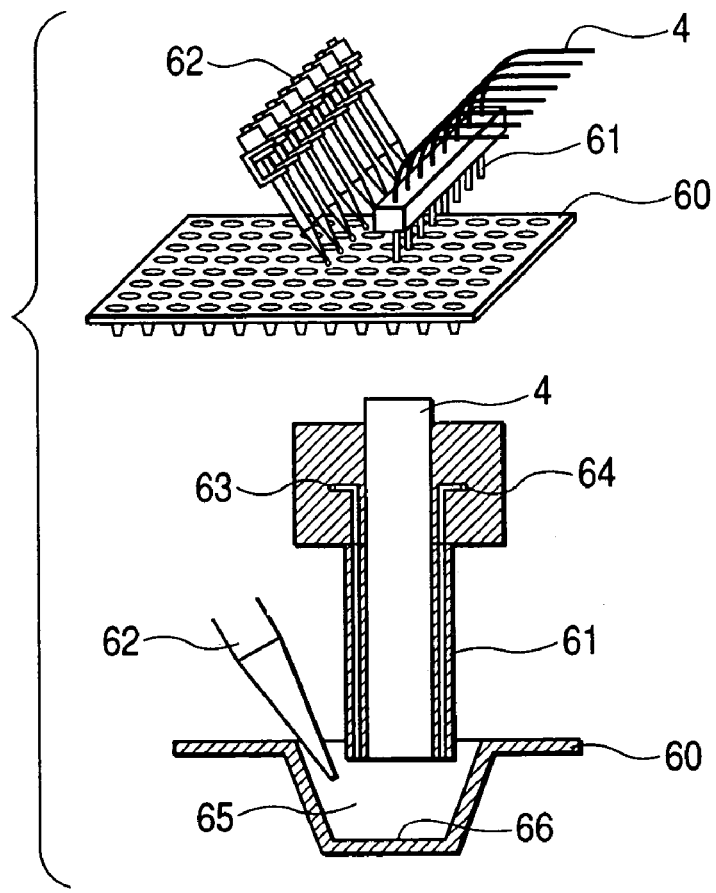
FIG. 6 is a longitudinal cross sectional view for a further embodiment of a sensor plate according to the invention.

FIG. 6 shows, in a vertical cross sectional view, a further embodiment of a sensor plate used in the measuring apparatus for biomolecule interaction according to the invention. A plurality of optical fibers 4 are disposed in an optical fiber guide 61 and the optical fibers 4 are branched as shown in FIG. 1 into measuring optical fibers 4A and light source optical fibers 4B, and the light source optical fibers 4B are connected with a light source, while the measuring optical fibers 4A are connected with a photo spectrometer, an A/D converter, and a data processing device.

Then, in this embodiment, a plurality of reaction vessels 65 (8 hole×12 rows) are formed in a sensor plate 60. The inner bottom for each of the reaction vessels 65 constitutes a fine particle sensor surface 66. Further, a buffer solution injection flow channel 63 and a discharge flow channel 64 are formed to the optical fiber guide 61, and the buffer solution can be injected through the buffer solution injection flow channel 63 to the reaction vessel 65 of the sensor plate 60. Further, the buffer solution or the specimen contained in the reaction vessel 65 can be discharged through the discharge flow channel 64 to the outside.

Then, the measuring operation is to be described. The specimen to be measured is injected to the reaction vessel 65 of the sensor plate 60 by a dispensing device 62. Further, spectral measurement is conducted from above the sensor plate 60 by using the optical fibers 4 supported by the optical fiber guide 61. To the reaction vessel 65 of the sensor plate 60, a buffer solution is previously injected, or a buffer solution is injected upon starting measurement from the buffer solution injection flow channel 63 passing through the optical fiber guide 61.

Then, while injecting the specimen to be measured from the dispensing device 62, a surplus buffer solution is sucked by the discharge flow channel 64 passing the inside of the optical fiber guide 61 and the inside of the reaction vessel 65 is replaced with the measuring specimen. In this case, when the biomolecules contained in the specimen are bonded with the ligand fixed on the fine particle sensor surface 66, the absorption spectrum at the fine particle sensor surface 66 changes and the signal of binding is measured through the optical fibers 4.

Then, a surplus liquid specimen is sucked by the discharge flow channel 64 while injecting the buffer solution from the buffer solution injection flow channel 63 and the inside of the reaction vessel 65 is replaced with the buffer solution. In this case, when the biomolecules bonded with the ligand fixed on the fine particle sensor surface 66 are dissociated, the absorption spectrum on the fine particle sensor surface 66 changes and the signal of dissociation is measured through the optical fibers 4.

Also this embodiment can provide a measuring apparatus for biomolecule interaction capable of automating optical measurement also including the deposition of the liquid specimen and the buffer solution to the fine metal particles and capable of processing a great amount of specimens in parallel in a short time although it is reduced in the size. In this embodiment, different form each of the embodiments described above, the structure of the sensor plate 60 is made relatively simple. However, in a case where the kind and the concentration of the specimen are intended to be changed on every measurement, this requires a not illustrated mechanism for charging individual specimen to be dispensing device 62.

According to the invention it is possible to provide a measuring apparatus for biomolecule interaction capable of automating optical measurement also including the deposition of the liquid specimen and the buffer solution to the fine metal particles and capable of processing a great amount of specimens in parallel in a short time although it is reduced in the size. According to the invention, it is possible to provide a measuring apparatus for biomolecule interaction of a simple structure capable of simultaneously measuring plural interactions of biomolecules and screening in the development of medicines, inspection of foods, etc. and medical diagnosis can be conducted easily in a great amount.

The sensor plate according to the present invention provides advantageous effects of preventing contamination of specimens and improving the measuring accuracy by separating sensors and specimens to be measured on every measuring conditions and adopting an easily replaceable structure, as well as shortening the measuring time for various conditions and specimens by facilitating the previous preparation. Further, it also provides an advantageous effect of reducing the number of parts to make the structure simple by the adoption of a structure where the sensor plate serves both as a specimen well and as a sensor. In addition, the measuring apparatus for biomolecule interaction shown in each of the embodiments described above can measure not only proteins but also DNA.

What is claimed is:

1. A measuring apparatus for biomolecule interaction comprising: a fine particle sensor device having at least one specimen vessel for containing a liquid specimen and having a fine particle sensor surface in which fine noble metal particles are arranged; a plurality of reaction vessels capable of containing a buffer solution or the liquid specimen; a dipping device for dipping the fine particle sensor surface of the at least one specimen vessel into the buffer solution or the liquid specimen contained in the reaction vessel; an optical measuring device for measuring the optical characteristics of the fine particle sensor surface; and a light irradiation device of irradiating a light to the fine particle sensor surface dipped in the buffer solution or the liquid specimen and guiding the reflected light to the optical measuring device; wherein the fine particle sensor surface is an exterior surface of the at least one specimen vessel and is capable of bonding to biomolecules in the specimen.

2. The measuring apparatus for biomolecule interaction according to claim 1, wherein the bottom of the reaction vessel is formed of a transparent member and a light from the light irradiation device is irradiated by way of the transparent member to the fine particle sensor surface.

3. The measuring apparatus for biomolecule interaction according to claim 2, wherein the dipping device is a device of moving the reaction vessel capable of approaching or receding the reaction vessel to and from the fine particle sensor surface.

4. The measuring apparatus for biomolecule interaction according to claim 2, wherein the fine particle sensor device has a pressurizing device for pressurizing a gas to move the liquid specimen contained in the specimen vessel to the reaction vessel.

5. The measuring apparatus for biomolecule interaction according to claim 4, wherein the reaction vessel has a buffer solution injection flow channel for injecting the buffer solution to the reaction vessel and a discharge flow channel for discharging the buffer solution or the liquid specimen contained in the reaction vessel from the reaction vessel, wherein the pressurizing device moves the liquid specimen contained in the specimen vessel to the reaction vessel when the fine particle sensor surface is inserted in the reaction vessel, and discharges the buffer solution contained in the reaction vessel from the discharge flow channel to the outside of the reaction vessel and replaces the buffer solution with the liquid specimen.

6. The measuring apparatus for biomolecule interaction according to claim 5, wherein the buffer solution is injected from the buffer solution injection flow channel to the reaction vessel to dissociate biomolecules bonded to the fine particle sensor surface, after replacing the buffer solution with the liquid specimen, and the dissociation process is measured by the optical measuring device receiving a light reflected form the fine particle sensor surface.

7. The measuring apparatus for biomolecule interaction according to claim 1, wherein a plurality of specimen vessels are arranged to form a sensor plate.

8. The measuring apparatus for biomolecule interaction according to claim 1, wherein the at least one specimen vessel contains a predetermined amount of the liquid specimen therein.

* * * * *